US008535316B2

(12) United States Patent
Lewis et al.

(10) Patent No.: US 8,535,316 B2
(45) Date of Patent: Sep. 17, 2013

(54) HOLLOW REAMER FOR MEDICAL APPLICATIONS (76) Inventors: Randall J. Lewis, Bethesda, MD (US); Christopher G. Sidebotham, Mendham, NJ (US)

( * ) Notice: Subject to any disclaimer, the term of this patent is extended or adjusted under 35 U.S.C. 154(b) by 1378 days.

(21) Appl. No.: 11/704,754

(22) Filed: Feb. 9, 2007

(65) Prior Publication Data
US 2008/0195103 A1 Aug. 14, 2008

(51) Int. Cl.
*A61B 17/00* (2006.01)
(52) U.S. Cl.
USPC ............................................................ 606/80
(58) Field of Classification Search
USPC ..................................................... 606/79–90
See application file for complete search history.

(56) References Cited

U.S. PATENT DOCUMENTS

| | | | | |
|---|---|---|---|---|
| 2,265,472 | A |  | 12/1941 | Campbel ........................ 175/407 |
| 4,116,200 | A |  | 9/1978 | Braun et al. ..................... 605/81 |
| 4,582,060 | A | * | 4/1986 | Bailey ............................ 606/186 |
| 4,811,632 | A |  | 3/1989 | Salyer ............................. 76/115 |
| 5,100,267 | A |  | 3/1992 | Salyer ............................ 407/54 |
| 5,116,165 | A |  | 5/1992 | Salyer ............................ 407/54 |
| 5,171,312 | A |  | 12/1992 | Salyer ............................ 606/81 |
| 5,171,313 | A |  | 12/1992 | Salyer ............................ 606/86 |
| 5,190,548 | A |  | 3/1993 | Davis .............................. 606/80 |
| 5,236,433 | A |  | 8/1993 | Salyer ............................ 606/91 |
| 5,282,804 | A |  | 2/1994 | Salyer ............................ 606/86 |
| 5,299,893 | A |  | 4/1994 | Salyer ............................ 407/54 |
| 5,376,092 | A | * | 12/1994 | Hein et al. ....................... 606/81 |
| 5,501,686 | A |  | 3/1996 | Salyer ............................. 696/79 |
| 5,549,613 | A |  | 8/1996 | Goble et al. ..................... 606/80 |
| 5,556,399 | A |  | 9/1996 | Huebner ......................... 606/80 |

(Continued)

FOREIGN PATENT DOCUMENTS

| | | | |
|---|---|---|---|
| DE | 3630069 C1 | * | 1/1988 |
| EP | 88401621.3 | * | 12/1988 |
| WO | WO 9007908 |  | 7/1990 |

OTHER PUBLICATIONS

"Effect of Flexible Drive Diameter and Reamer Design on the Increase of Pressure in the Medullary Cavity During reaming", Mueller et al., PubMed (1993) http://www.ncbi.nlm.nih.gov/entrez/query.fcgi?db=pubmed&cmd=Retrieve&dopt=AbstractPlus&list_uids=8168875&query_hl=2&itool=pubmed_Brief.

(Continued)

*Primary Examiner* — Thomas C. Barrett
*Assistant Examiner* — Matthew Lawson
(74) *Attorney, Agent, or Firm* — Ernest D. Buff; Ernest D. Buff & Assoc. LLC; Margaret A. LaCroix, Esq.

(57) ABSTRACT

A reamer for medical applications includes an elongated shaft portion and a disposable hollow cutter assembly. The shaft portion's distal end has a coupling portion appointed for attachment to a drilling device, and the proximal end has a threaded portion. The cutter assembly includes a disposable hollow cutter sleeve and a pilot tip. The cutter sleeve has an outer surface and a hollow construction, and is preferably appointed for a single use. In addition, the disposable cutter sleeve portion has a plurality of cutting teeth and a plurality of apertures on the outer surface. The pilot tip has a threaded inner surface and is attached to the disposable cutter sleeve. The cutter assembly is adapted to slide over the proximal end of the shaft portion, thereby enabling the pilot tip to be threaded with the threaded portion of the proximal end of the shaft portion.

15 Claims, 11 Drawing Sheets

(56) References Cited

U.S. PATENT DOCUMENTS

| | | | |
|---|---|---|---|
| 5,690,634 A | 11/1997 | Muller et al. | 606/80 |
| 5,709,688 A | 1/1998 | Salyer | 606/81 |
| 5,755,719 A | 5/1998 | Frieze | 606/81 |
| 5,817,096 A | 10/1998 | Salyer | 606/81 |
| 5,902,321 A | 5/1999 | Caspari et al. | 606/232 |
| 5,908,423 A * | 6/1999 | Kashuba et al. | 606/80 |
| 5,931,841 A | 8/1999 | Ralph | 606/85 |
| 5,954,671 A | 9/1999 | O'Neill | 600/567 |
| 5,976,144 A | 11/1999 | Fishbein et al. | 606/80 |
| 5,980,170 A | 11/1999 | Salyer | 408/239 R |
| 6,001,105 A | 12/1999 | Salyer | 606/81 |
| 6,162,226 A * | 12/2000 | DeCarlo et al. | 606/80 |
| 6,168,600 B1 | 1/2001 | Grace et al. | 606/81 |
| 6,193,722 B1 | 2/2001 | Zech et al. | 606/79 |
| 6,245,074 B1 * | 6/2001 | Allard et al. | 606/80 |
| 6,332,886 B1 | 12/2001 | Green et al. | 606/80 |
| 6,409,732 B1 | 6/2002 | Salyer | 606/91 |
| 6,428,543 B1 | 8/2002 | Salyer | 606/81 |
| 6,451,023 B1 | 9/2002 | Salazar et al. | 606/86 |
| 6,578,635 B1 | 6/2003 | Hailey | 166/277 |
| 6,730,094 B2 | 5/2004 | Salyer et al. | 606/80 |
| 6,875,217 B2 | 4/2005 | Wolford | 606/81 |
| 7,074,224 B2 | 7/2006 | Daniels et al. | 606/80 |
| 7,229,078 B2 * | 6/2007 | Lechot | 279/93 |
| 2003/0181916 A1 | 9/2003 | Wolford | 606/81 |
| 2003/0212401 A1 | 11/2003 | Nordman | 606/80 |
| 2004/0267266 A1 * | 12/2004 | Daniels et al. | 606/80 |
| 2004/0267267 A1 * | 12/2004 | Daniels et al. | 606/80 |
| 2005/0113836 A1 | 5/2005 | Lozier et al. | 606/80 |
| 2006/0004371 A1 | 1/2006 | Williams et al. | 606/80 |
| 2006/0004461 A1 * | 1/2006 | Justin et al. | 623/20.34 |
| 2006/0025774 A1 * | 2/2006 | Fishbein et al. | 606/81 |
| 2006/0095041 A1 | 5/2006 | Fehlbaum et al. | 606/81 |
| 2006/0106393 A1 * | 5/2006 | Huebner et al. | 606/80 |
| 2006/0116688 A1 | 6/2006 | Boyd et al. | 606/90 |
| 2006/0184174 A1 | 8/2006 | Harris et al. | 606/80 |
| 2006/0229625 A1 * | 10/2006 | Truckai et al. | 606/79 |
| 2006/0235539 A1 | 10/2006 | Blunn et al. | 623/22.12 |
| 2006/0264956 A1 | 11/2006 | Orbay et al. | 606/80 |
| 2007/0088361 A1 * | 4/2007 | Ho | 606/80 |
| 2007/0233131 A1 * | 10/2007 | Song et al. | 606/79 |

OTHER PUBLICATIONS

"Single Use Sterile Power Equipment", Orthomedix.com, at http://www.orthomedex.com/index.html.

* cited by examiner

Figure 1

Prior Art

HOLLOW REAMER FOR MEDICAL APPLICATIONS

BACKGROUND OF THE INVENTION

1. Field of the Invention

The present invention relates to a hollow reamer for medical applications; and more particularly, to a hollow reamer having a disposable cutter assembly which can be attached to a reusable shaft portion.

2. Description of the Prior Art

Reaming of the internal canal of bones is required in many surgical procedures of orthopedic surgery. These procedures include hip replacement, knee replacement and shoulder replacement. Reamers are also used in procedures that involve the internal fixation of fractures. Prior art reamers typically fall into two major classes: rigid and flexible shaft. Typically, reaming of the internal bone canal is achieved through utilization of a solid cylindrical or tapered reamer. Solid cylindrical or tapered reamers currently utilized are required to cut both cancellous bone (spongy bone) and cortical bone (hard bone). Cortical bone is generally denser and stronger, requiring an efficient cutter to machine the canal for a proper fit of the implant. Conventional reamers can cut cortical bone initially but can quickly dull after a single use, or at best a few uses. Once the reamer has dull cutting edges, it reduces the efficiency of bone cutting and in addition generates sufficient friction/heat to damage or kill the surrounding bone. These prior art solid cylindrical or tapered reamers are intended for multiple uses and therefore become less efficient after each surgery, resulting in poor cutting performance and bone necrosis.

There remains a need in the art for a hollow reamer for medical applications having a disposable hollow cutter assembly which can be attached to a reusable shaft portion that provides means for reaming of the internal canal of bones whereby after one or more uses of the reamer a new hollow cutter assembly is utilized and the old hollow cutter assembly is discarded.

SUMMARY OF THE INVENTION

The present invention provides a hollow reamer for medical applications having a disposable cutter assembly which can be attached to a reusable shaft portion. Preferably, a fresh cutter assembly is used with each new application. Alternatively, the cutter assembly is used several times and, after it has become worn, is discarded. The cutter assembly includes a plurality of apertures and is hollow to allow space for bone debris. This therefore reduces heat generated during cutting by removing the bone debris from the outer surface of the cutter to the inside of the cutter, and further provides space for bone debris to be collected and later removed for bone grafting for the specific surgical procedure. A further advantage of the hollow design is that by allowing the removal of the bone debris from the outer surface of the cutter to the inside of the cutter, the reamer is less likely to raise the intramedulary pressure in the long bone being reamed, thereby lessening the chance of fat embolism during these procedures.

Generally stated, the reamer for medical applications comprises: (a) a shaft portion having an elongated body with a distal end and a proximal end, said distal end having a coupling portion appointed for attachment of said reamer to a drilling device, said proximal end having a threaded portion; and (b) a disposable hollow cutter assembly comprising: (1) a disposable hollow cutter sleeve portion having an outer surface and a hollow construction, said disposable hollow cutter sleeve portion further comprising a plurality of cutting teeth and a plurality of apertures on said outer surface; and (2) a pilot tip having a threaded inner surface and being attached to said disposable hollow cutter sleeve portion; said disposable hollow cutter assembly being adapted to slide over said proximal end of said elongated shaft portion and extend over a portion of said elongated body thereof, thereby enabling said pilot tip to be threaded with said threaded portion of said proximal end of said shaft portion.

The present invention solves the problems associated with the reuse of prior art reamers. In accordance with the present invention, the hollow reamer for medical applications has a disposable cutter assembly which can be attached to a reusable shaft portion that allows for a fresh cutter assembly to be used with each new application of the reamer. The hollow reamer of the present invention reduces heat during its application and is more efficient and safe when compared to prior art reamers.

BRIEF DESCRIPTION OF DRAWINGS

The invention will be more fully understood and further advantages will become apparent when reference is had to the following detailed description of the preferred embodiments and the accompanying drawings, in which.

DESCRIPTION OF THE PREFERRED EMBODIMENTS

Figure 1:
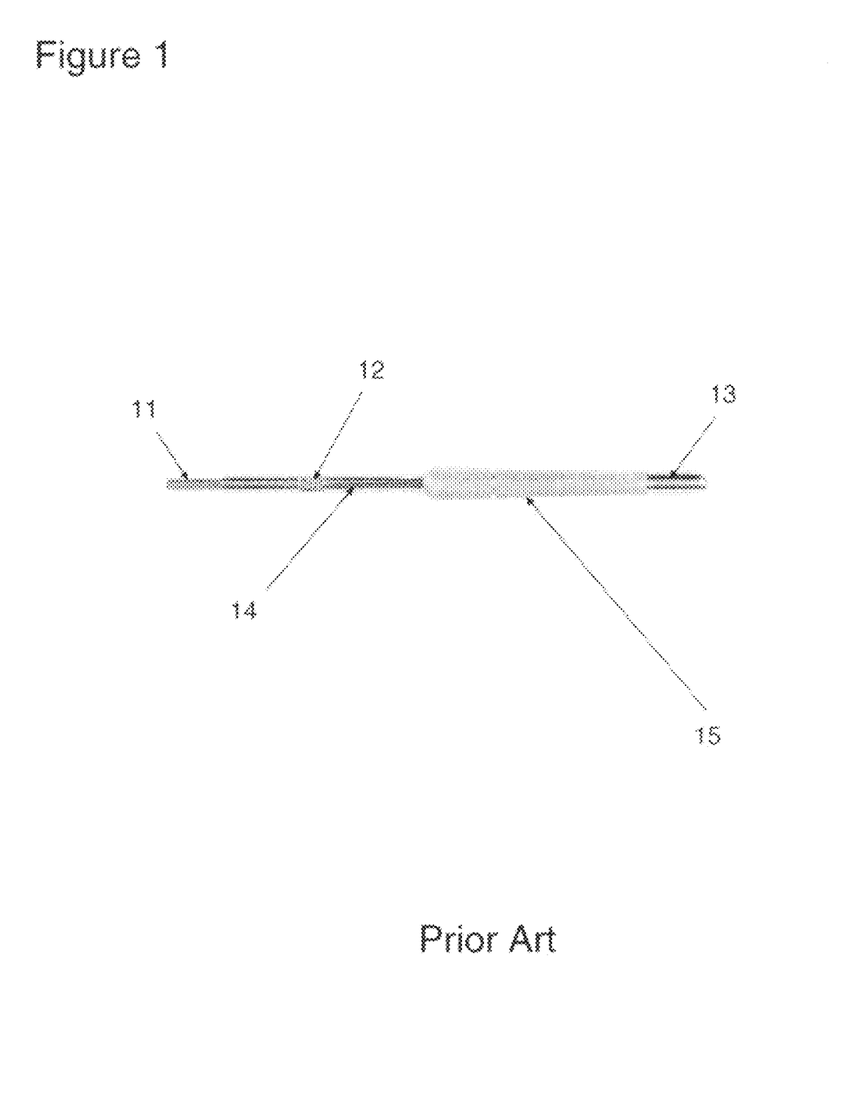
FIG. 1 is a perspective view depicting a medical tapered reamer found in the prior art.

Reaming of the internal canal of bones is required in many surgical procedures of orthopedic surgery. These procedures include hip replacement, knee replacement and shoulder replacement. Other surgical procedures that see the use of reamers include internal fixation procedures for fractures. Typically, reaming of the internal bone canal is achieved through utilization of a solid cylindrical or tapered reamer, illustrated in FIG. 1. Prior art reamers typically include a driver coupling 11 (shown as a Jacob chuck connector), a size designation 12, a pilot tip 13, a shaft 14, and cutting flutes 15. FIG. 1 shows a tapered reamer, however cylindrical reamers of similar design also exist in the prior art. Those solid cylindrical or tapered reamers currently utilized are required to cut both cancellous bone (spongy bone) and cortical bone (hard bone). Cortical bone is generally denser and stronger, requiring an efficient cutter to machine the canal for a proper fit of the implant. Conventional reamers can cut cortical bone initially but can quickly dull after a single use, or at best a few uses. Once the reamer has dull cutting edges, it reduces the efficiency of bone cutting and in addition generates sufficient friction/heat to damage or kill the surrounding bone. Currently utilized solid cylindrical or tapered reamers are intended for multiple uses and therefore become less efficient after each surgery, resulting in poor cutting performance and bone necrosis.

Figure 2:
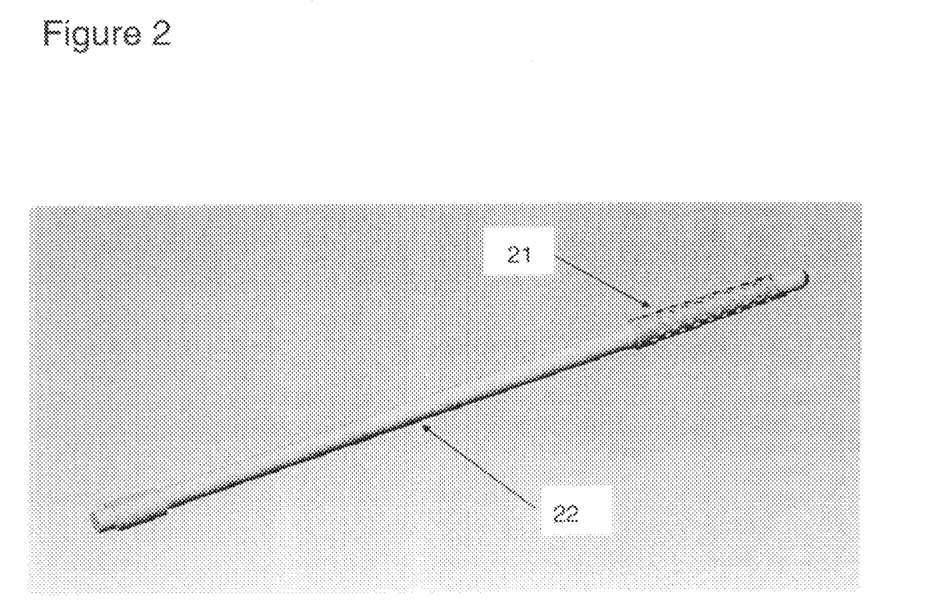
FIG. 2 is a perspective view depicting a hollow tapered reamer in accordance with the invention.

FIG. 2 depicts the hollow reamer assembly of the present invention which provides hollow reamers appointed for use in medical applications. The hollow cutter assemblies are disposable, so that the cutting performance of the hollow reamer is not compromised through repeated use. Several improvements towards the clinical problems seen with prior art reamers are overcome through utilization of the hollow reamers herein. Novel design features of the hollow reamers of the present invention and improvements to prior art reamers are multifaceted and include a reusable shaft 22 with a disposable hollow cutter assembly 21. Preferably, the hollow cutter assembly 21 is discarded after a single use to ensure a sharp cutter during surgery. Alternatively, the hollow cutter assembly is used several times and after becoming worn is discarded. Various techniques may be used to determine if the hollow cutter assembly is worn enough that it requires disposal. Such techniques may include measurements of the sharpness of the cutter assembly. Moreover, when dealing with revision hip surgery, the hollow reamers have also been designed to cut bone cement (PMMA) in a more efficient manner by providing internal space to capture the debris and thereby reducing both the cutting temperature and time required to remove the remnant cement mantle. Both these features are important in reducing heat to the bone and reducing O.R. (operating room) time required for revision surgery. FIG. 2 illustrates a hollow reamer having a tapered cutter portion of the present invention. Alternatively, a hollow reamer having a cylindrical design may be utilized. The hollow reamer comprises a shaft portion 22 and a disposable hollow cutter assembly 21. The shaft portion 22 can either be solid or cannulated.

Figure 3A:
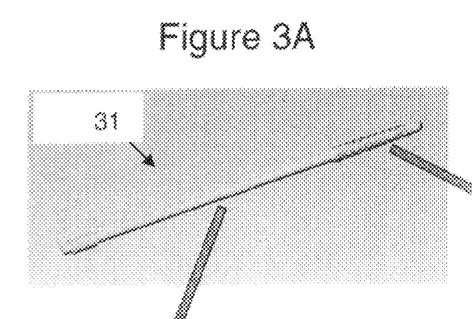
FIGS. 3A, 3B, 3C, collectively, provide an assembly view depicting the hollow reamer in FIG. 3A that is formed by the disposable hollow cutter in FIG. 3B and reusable shaft in FIG. 3C in accordance with the invention.
Figure 3B:
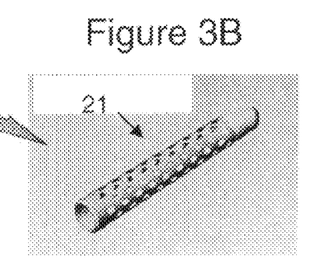
Figure 3C:
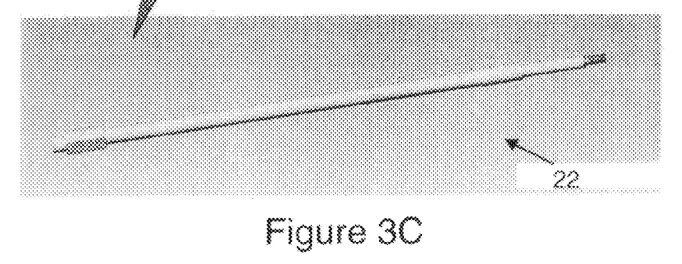

FIGS. 3A, 3B, 3C, collectively, provide an assembly view depicting the hollow reamer in FIG. 3A that is formed by the disposable hollow cutter in FIG. 3B and reusable shaft in FIG. 3C in accordance with the invention. FIG. 3A depicts the modular design of the hollow reamer at 31. FIG. 3C depicts a reusable reamer shaft 22. The reamer shaft 22 may be flexible or rigid depending on the particular medical application. FIG. 3B depicts a disposable, one-time use hollow cutter assembly 21.

Figure 4A:
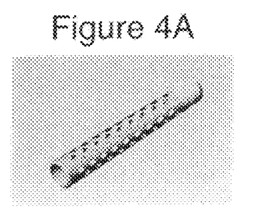
FIG. 4A is a perspective view depicting the disposable hollow cutter in accordance with the invention.
Figure 4B:
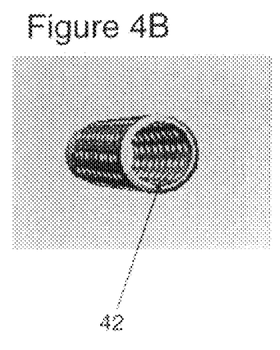
FIG. 4B is a side view depicting the disposable hollow cutter in accordance with the invention.
Figure 4C:
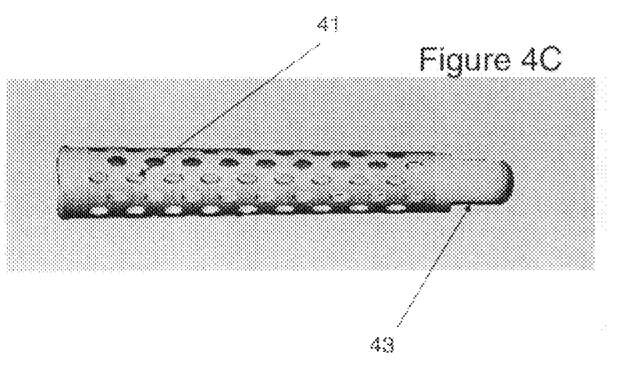
FIG. 4C is a front view depicting the disposable hollow cutter in accordance with the invention.

FIG. 4A is a perspective view depicting the disposable hollow cutter in accordance with the invention. FIG. 4B is a side view depicting the disposable hollow cutter in accordance with the invention. FIG. 4C is a front view depicting the disposable hollow cutter in accordance with the invention.

FIG. 4C depicts the disposable hollow cutter assembly which comprises: (i) a disposable hollow cutter sleeve portion having an outer surface and a hollow construction, the disposable hollow cutter sleeve portion further comprising a plurality of cutting teeth 41 and a plurality of apertures (also at 41) on the outer surface; and (ii) a pilot tip 43 having a threaded inner surface and being attached to the disposable hollow cutter sleeve portion. The non-cutting pilot tip 43 is designed for guidance, and the tip 43 matches the diameter of the previous cutter sleeve end to achieve this guidance feature. The pilot tip 43 further helps to keep each successive reamer centered, thereby resisting the tendency of the reamer to drift and cut eccentrically, particularly when there is eccentric cement in the canal. Preferably, the pilot tip 43 is tapered at about the same angle as the hollow cutter sleeve. Alternatively, the pilot tip 43 is generally cylindrical. Preferably, the hollow cutter assembly is discarded after a single use to ensure a sharp, efficient cutter for every surgery. Alternatively, the hollow cutter assembly is used several times and, upon becoming worn, is discarded. FIG. 4B further depicts the hollow cutter which provides space 42 for bone debris offering multiple benefits, including reducing heat generated during cutting by removing the bone debris from the outer surface of the cutter to the inside of the cutter and providing space 42 for bone debris to be collected and later removed for bone grafting for the specific surgical procedure. A further advantage of the hollow design is that by allowing the removal of the bone debris from the outer surface of the cutter to the inside of the cutter, the reamer is less likely to raise the intramedulary pressure in the long bone being reamed, thereby lessening the chance of fat embolism during these procedures. The hollow cutter sleeve is provided with a plurality of apertures 41 on its outer surface. Preferably, the cutting teeth 41 protrude from the outer surface of the disposable hollow cutter sleeve, consequently forming the plurality of apertures. Alternatively, the plurality of apertures can be separate and distinct from the cutting teeth on the outer surface of the disposable hollow cutter sleeve.

Figure 5:
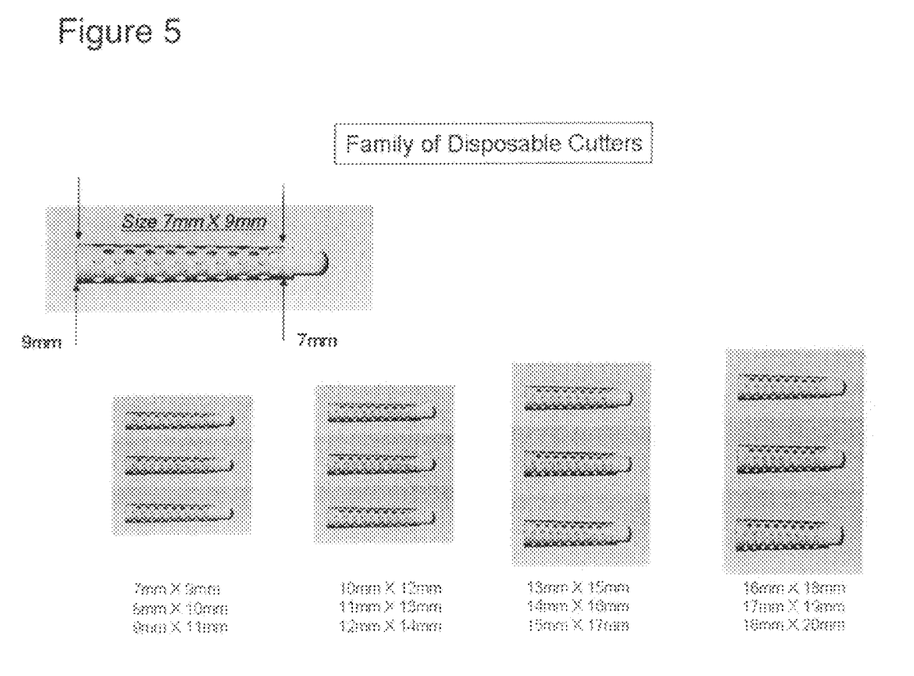
FIG. 5 is a perspective view depicting a family of disposable hollow cutters in accordance with the invention.

FIG. 5 illustrates a family of disposable cutter assemblies. The family of disposable cutter assemblies addresses a wide range of bone sizes, including sizes ranging from 7 mm through 20 mm in one (1) mm increments; and being tapered and having a 7 mm tapering to a larger diameter in one (1) to three (3) mm increments and having size options from a 7 mm base dimension to a 20 mm base dimension in one (1) mm increments. Preferably, and as shown in FIG. 5, the hollow cutter assemblies are tapered. Alternatively, the hollow cutter assemblies are cylindrical and have diameters ranging from 7 mm through 20 mm. Preferably, there are provided two shafts of each size in the instrument set, thereby allowing the surgeon to go back one size during the procedure, if necessary, without having to break off the disposable cutter.

Figure 6:
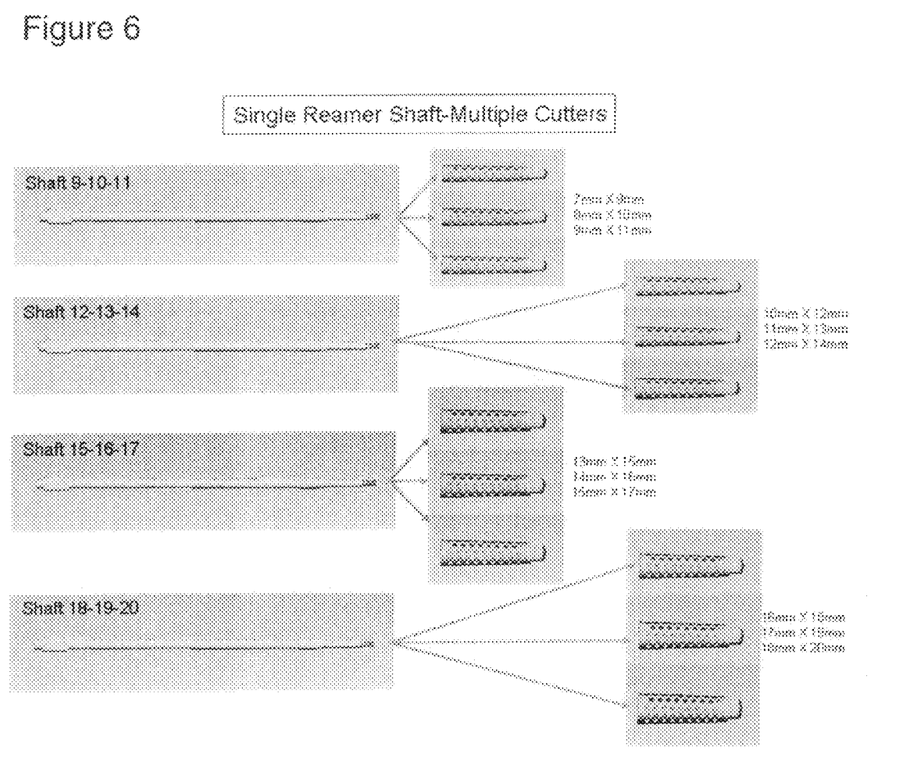
FIG. 6 is a perspective view depicting the ability of a single reamer shaft to work with a plurality of various-sized disposable hollow cutters.

Multiple disposable cutter assemblies can be attached to a single shaft, as is illustrated in FIG. 6. Preferably, a single shaft will attach to at least three different sized disposable hollow cutter assemblies. This provides for the ability to combine various sized shafts with various sized disposable hollow cutter assemblies.

Figure 7:
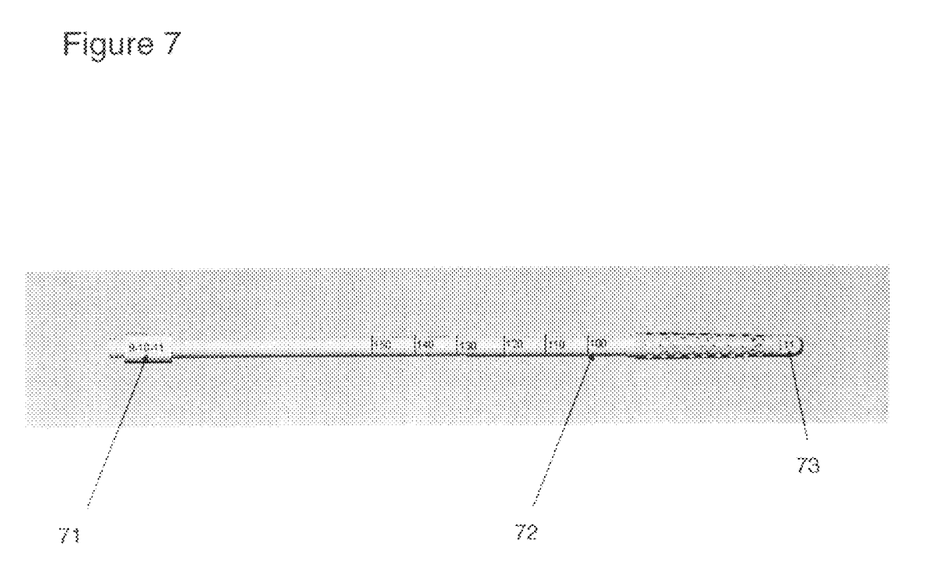
FIG. 7 is a perspective view depicting a reusable shaft with a plurality of graduations to determine the depth of the disposable hollow cutter assembly in the canal of the bone during use.

FIG. 7 shows the reamer shaft appointed with graduated markings 72. The reamer shaft incorporates graduations 72 to determine the depth of insertion of the cutter assembly into the canal of the bone. The reamer shaft further incorporates markings 71 to identify the proper assembly between the shaft and the cutter assembly. Alternatively, this method could be further enhanced through color coding the shafts and the disposable hollow cutters. A shaft size designation marking 71 informs the user as to what sized disposable hollow cutter assemblies will fit the shaft. A cutter assembly size designation 73 is indicated on the pilot tip of the disposable hollow cutter assembly.

Figure 8:
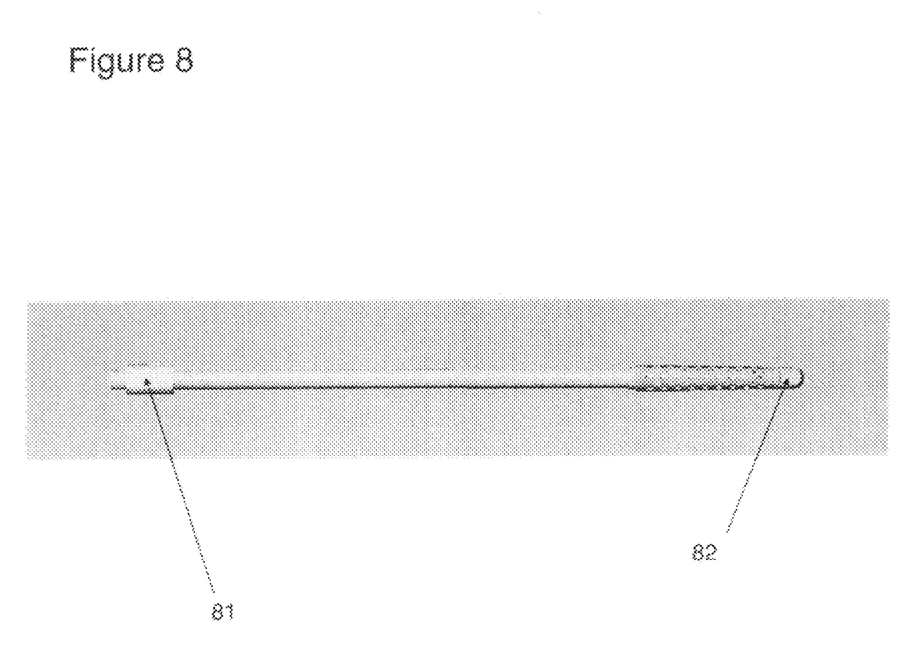
FIG. 8 is a perspective view depicting a hollow tapered reamer in accordance with the invention.

FIG. 8 illustrates the shaft cutter assembly, showing flats on the reamer shaft end and flats on the disposable cutter assembly pilot tip, which are provided to facilitate assembly of the disposable hollow cutter assembly to the shaft using simple wrenches found in the prior art.

Figure 9:
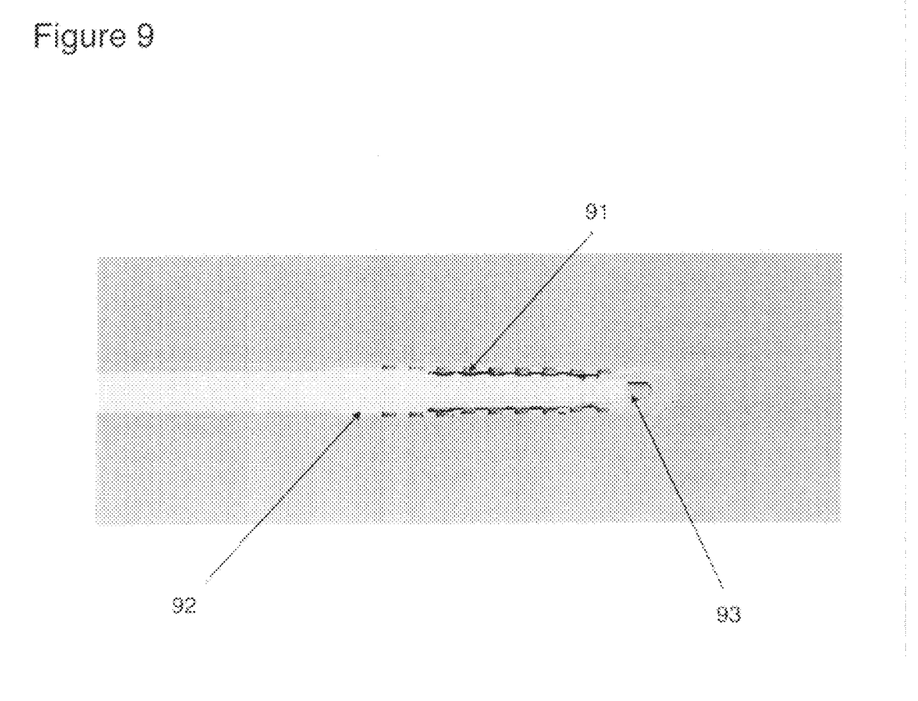
FIG. 9 is a perspective view depicting a tapered portion of the elongated body of said shaft portion for securing said disposable hollow cutter assembly and a left-hand thread for assembly into the pilot tip.

FIG. 9 shows an embodiment of the shaft/disposable hollow cutter assembly wherein the inner surface of the pilot tip 93 is threaded. One method for assembling the disposable cutter assembly 91 to the shaft incorporates a left-hand thread on the end of the shaft and a left-hand thread in the inner surface of the pilot tip of the disposable hollow cutter assembly. With this assembly arrangement, the assembly tightens during operation (hand or power reaming is right-hand rotation) thereby providing stability of the cutter assembly 91 to the shaft. The assembly method between the reamer shaft and the disposable cutter assembly 91 is further shown in FIG. 9, where the reamer shaft has a taper 92 incorporated into the body of the shaft, which closely mates with the internal taper of the hollow disposable cutter sleeve 91, thereby establishing stability to the opposite end of the cutter from the thread attachment.

Figure 10:
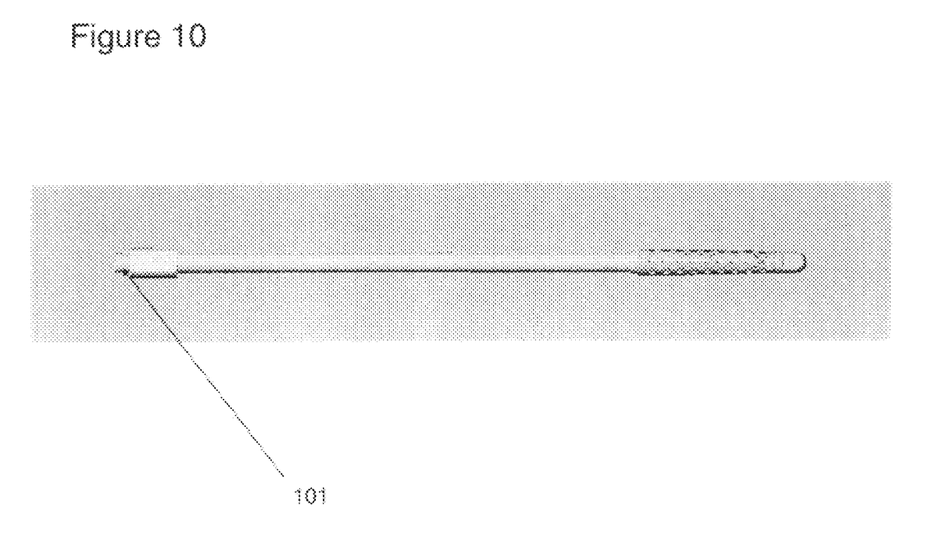
FIG. 10 is a perspective view depicting a coupling portion appointed for attachment of the reamer to a drilling device.

FIG. 10 illustrates the shaft drive coupling. A reamer shaft having a driver end 101 compatible with currently available hand and power instruments in the medical field is provided. The hollow reamer could also be coupled with a flexible drive shaft.

Figure 11A:
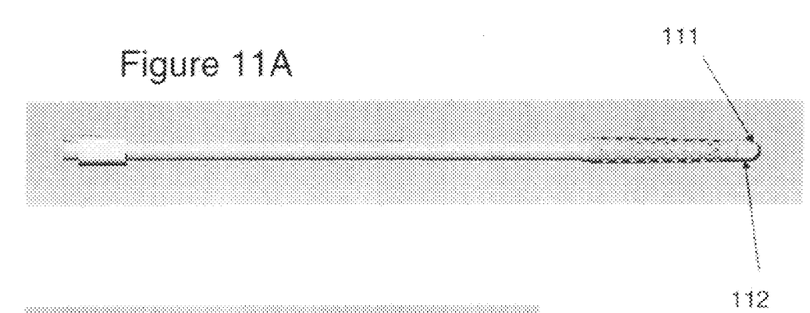
FIGS. 11A and 11B each show a perspective view depicting a break-away feature of the pilot tip during disassembly to prevent reuse of the disposable hollow cutter.
Figure 11B:
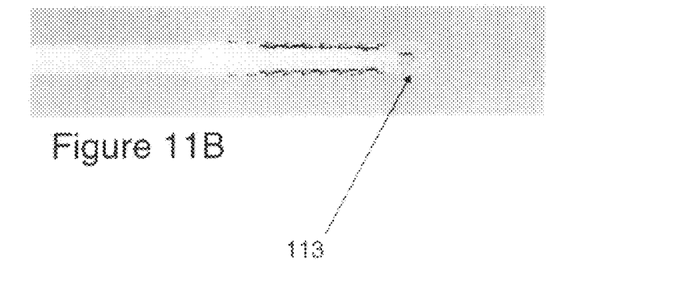

FIGS. 11A and 11B each illustrate an alternative embodiment of the disposable hollow cutter assembly which incorporates a disposable hollow cutter break-away feature which prevents reuse of the disposable hollow cutter assembly. The pilot tip 111 of the disposable hollow cutter assembly includes a flat portion 112 in order to enable the assembly and disassembly of the disposable hollow cutter assembly to the shaft by using a simple wrench or the like. The disposable hollow cutter assembly is assembled with a wrench. Following use of the disposable hollow cutter assembly, it is disassembled from the shaft by using the wrench. The disposable hollow cutter assembly is preferably manufactured in such a manner so that the break away torque that is required for disassembling the disposable hollow cutter assembly from the shaft will cause the pilot tip 113 to shear away from the hollow cutter sleeve portion. Then, the pilot tip may be unthreaded from the drive shaft, and the hollow cutter sleeve portion may be slid off the end of the shaft. Once the reamer is disassembled in this manner, the disposable hollow cutter assembly can not be reused. Therefore, the optional break away feature prevents the re-use of the same disposable hollow cutter assembly, thereby assuring the proper function that can only be provided by the use of a new disposable hollow cutter assembly.

Having thus described the invention in rather full detail, it will be understood that such detail need not be strictly adhered to, but that additional changes and modifications may suggest themselves to one skilled in the art, all falling within the scope of the invention as defined by the subjoined claims.

What is claimed is:

1. A reamer for medical applications, comprising:
    a. a shaft portion having an elongated body with a distal end and a proximal end, said distal end having a coupling portion appointed for attachment of said reamer to a drilling device, said proximal end having a threaded portion; and
    b. a disposable hollow cutter assembly comprising:
        1. a cylindrical disposable hollow cutter sleeve portion having an outer surface and a hollow construction forming a hollow interior space adapted to collect bone debris, said disposable hollow cutter sleeve portion further comprising a plurality of cutting teeth and a plurality of apertures on said outer surface leading into said hollow interior space; and
        2. a non-cutting pilot tip having a threaded inner surface and being attached to said disposable hollow cutter sleeve portion;
        3. said disposable hollow cutter assembly being adapted to slide over said proximal end of said elongated body and extend over a portion of said elongated body thereof, thereby enabling said non-cutting pilot tip to be threaded with said threaded portion of said proximal end of said shaft portion;
        4. said plurality of apertures being adapted to remove bone debris from said outer surface of said hollow cutter sleeve portion to be collected within said hollow interior space within said cutter sleeve.

2. A reamer for medical applications as recited by claim 1, wherein said shaft portion is reusable.

3. A reamer for medical applications as recited by claim 1, wherein said threaded portion of said proximal end of said shaft portion has a left-hand thread for assembly into said pilot tip.

4. A reamer for medical applications as recited by claim 1, wherein said elongated body of said shaft portion further comprises a plurality of graduations to determine the depth of said disposable hollow cutter assembly in a canal of a bone during use.

5. A reamer for medical applications as recited by claim 1, wherein said elongated body of said shaft portion further comprises a marking to indicate its size.

6. A reamer for medical applications as recited by claim 1, wherein said pilot tip further comprises a marking to indicate its size.

7. A reamer for medical applications as recited by claim 1, wherein said elongated body of said shaft portion further comprises a tapered portion for securing said disposable hollow cutter assembly.

8. A reamer for medical applications as recited by claim 1, wherein said disposable hollow cutter assembly is manufactured so that said pilot tip is sheared from said disposable hollow cutter sleeve portion when removing said disposable hollow cutter assembly from said shaft portion, in order to prevent reuse thereof.

9. A reamer for medical applications as recited by claim 1, wherein said pilot tip includes a flat portion being appointed for insertion with a wrench.

10. A reamer for medical applications as recited by claim 1, wherein said disposable hollow cutter sleeve portion is appointed for a single, one-time use.

11. A reamer for medical applications as recited by claim 1, wherein said disposable hollow cutter sleeve portion is appointed for more than a single use depending on the amount of damage to said cutter sleeve portion after its initial use.

12. A reamer for medical applications as recited by claim 1, wherein said shaft portion is cannulated.

13. A reamer for medical applications as recited by claim 1, wherein said shaft portion is solid.

14. A reamer for medical applications as recited by claim 1, wherein said shaft portion is flexible.

15. A reamer for medical applications as recited by claim 1, wherein said shaft portion is rigid.

* * * * *